(12) United States Patent
Reitzig et al.

(10) Patent No.: US 8,821,552 B2
(45) Date of Patent: Sep. 2, 2014

(54) SPINAL-COLUMN PLATE IMPLANT

(75) Inventors: Cliff-Georg Reitzig, Rietheim-Weilheim (DE); Stephan Eckhof, Rietheim-Weilheim (DE); Barbara Schweizer, Wurmlingen (DE)

(73) Assignee: Ulrich GmbH & Co. KG, Ulm (DE)

( * ) Notice: Subject to any disclaimer, the term of this patent is extended or adjusted under 35 U.S.C. 154(b) by 888 days.

(21) Appl. No.: 12/522,585

(22) PCT Filed: Jan. 22, 2008

(86) PCT No.: PCT/DE2008/000100
§ 371 (c)(1),
(2), (4) Date: Jan. 20, 2010

(87) PCT Pub. No.: WO2008/092422
PCT Pub. Date: Aug. 7, 2008

(65) Prior Publication Data
US 2010/0121328 A1 May 13, 2010

(30) Foreign Application Priority Data
Jan. 30, 2007 (DE) .................... 20 2007 001 585 U

(51) Int. Cl.
*A61B 17/66* (2006.01)
*A61B 17/70* (2006.01)
*A61B 17/80* (2006.01)
*A61B 19/00* (2006.01)

(52) U.S. Cl.
CPC ....... *A61B 17/7059* (2013.01); *A61B 2019/444* (2013.01); *A61B 17/8023* (2013.01)
USPC ........................................... 606/282; 606/71

(58) Field of Classification Search
USPC .............. 606/70, 71, 280, 282, 291, 295, 296
See application file for complete search history.

(56) References Cited

U.S. PATENT DOCUMENTS

| 5,616,142 | A | 4/1997 | Yuan ................................ 606/61 |
| 6,238,396 | B1 * | 5/2001 | Lombardo .................. 606/86 A |
| 6,306,136 | B1 | 10/2001 | Baccelli .......................... 606/61 |
| 6,503,250 | B2 * | 1/2003 | Paul ............................... 606/279 |
| 6,602,255 | B1 * | 8/2003 | Campbell et al. ............. 606/290 |
| 6,679,883 | B2 * | 1/2004 | Hawkes et al. ............... 606/279 |
| 2002/0183755 | A1 * | 12/2002 | Michelson ....................... 606/71 |
| 2004/0215195 | A1 | 10/2004 | Shipp .............................. 606/69 |
| 2005/0216010 | A1 | 9/2005 | Michelson ....................... 606/69 |
| 2005/0216011 | A1 * | 9/2005 | Paul ................................ 606/69 |
| 2005/0240187 | A1 * | 10/2005 | Huebner et al. ................ 606/69 |

* cited by examiner

*Primary Examiner* — Christian Sevilla
(74) *Attorney, Agent, or Firm* — Andrew Wilford

(57) ABSTRACT

The invention relates to a plate-implant for use in osteosynthesis, comprising at least one first plate component with throughbores for receiving fastening screws and a connection means, at least one second plate component with throughbores for receiving fastening screws and a receiving means for receiving a connection means. According to the invention, each plate component is slidable in one direction relative to the other plate component, the plate components being provided with a device limiting their slide path relative to each other. The device comprises a clamping screw (18) having a thread and a screw head and, in the mounted state of the two plate components (2, 3), the thread cooperates with the connection means (5) and the screw head with a longitudinal borehole (14) provided in the second plate component (3) in such a way that a clamping effect is obtained between the screw head and the longitudinal borehole (14) and between the connection means (5) and the receiving means (6).

5 Claims, 17 Drawing Sheets

SPINAL-COLUMN PLATE IMPLANT

CROSS REFERENCE TO RELATED APPLICATIONS

This application is the US-national stage of PCT application PCT/DE2008/000100, filed 22 Jan. 2008, published 7 Aug. 2008 as WO2008/092422, and claiming the priority of German patent application 202007001585.2 itself filed 30 Jan. 2007, whose entire disclosures are herewith incorporated by reference.

FIELD OF THE INVENTION

The invention relates to a plate implant that in its basic configuration comprises a first plate and a second plate. The first plate has bores for receiving fastening screws and a connector. The other, second plate has a seat for receiving a connector and bores for receiving fastening screws. Each of the plates is borne slidable in one direction relative to the other plate and the plates are provided with formations that limit their sliding relative to one another.

PRIOR ART

Osteosynthesis is a method for treating bone fractures and other bone injuries in which in particular implants that comprise metal are used. The goal is to fix the position of the bone fragments that belong together in a normal position (repositioning). As a rule surgical care involves attaching metal plates and fastening screws to the bone or, in particular for fractures of the shaft of the major long bones, it involves inserting long rods that fit in the medullary cavity along the axis of the bone.

Special techniques are known in particular for joining bones of the cervical vertebras. These techniques are typically employed for conditions that may derive from a cervicobrachial syndrome, but they can also be used for a degenerative spinal column, as well. The techniques applied for cervicobrachial syndromes are based on surgically reducing or eliminating so-called craniocervical instability by adding plate implants. To this end, plate-like elements that include a plurality of bores for receiving fastening screws are attached to the side of the spinal column that faces away from the body so that a plurality of consecutive vertebras are joined to one another using the fastening screws.

In particular when the plate implants are being fastened there is the problem that as a rule the spacing between consecutive vertebras is frequently different so that a number of plate implants of different lengths must be kept in stock in different embodiments.

In order to prevent this situation, U.S. Pat. No. 5,616,142 (Yuan Hansen A (US); Lin Chin-I (US)) 1 Apr. 1997 describes an implant that comprises two plates, each of which has seat for receiving a connector of an intermediate plate. The connectors themselves can slide in the seat so that the spacing between the two plates can be variable. The plates themselves have bores into which the fastening screws can be inserted. As soon as the spacing between the two plates is fixed, the intermediate plate is fixed to the plates so that the result is a rigid plate implant that cannot be moved. This results in the property of simple adaptation to different intermediate spaces between the bones or vertebras.

A plate implant, in particular a bone plate for use on the anterior side of a spinal column, is known from WO 1999/004718 (Dimso Distribution Medicale du Sud Ouest) 4 Feb. 1999 [U.S. Pat. No. 6,306,136]. This bone implant is intended especially for use on the anterior cervical vertebras. It comprises two plates that slide toward one another, each of which has bores for receiving fastening screws. Furthermore, each has a connector or a seat so that both plates can slide toward one another. Due to sliding movement, the spacing between the fastening screws for each plate may be selected so that the fastening screws find sufficient purchase in the bone. If the position is selected appropriately, the two bones or vertebras can be pressed together so that there is a corresponding sliding movement by the two plate implants. When the desired position has been attained, the sliding can be stopped and thus completely blocked by inserting a fixing screw so that a positive-fit and force-transmitting implant results.

DISADVANTAGES OF THE PRIOR ART

The term "settling" or "sinking" (hereinafter referred to as "settling") shall be understood to be migration by the bones or vertebras that degenerate due to non-loading (because of the implant being attached) and change their position accordingly. A placeholder is inserted between the vertebras before a plate implant is attached. Placeholders can comprise exogenous material or endogenous material (for instance bone). This placeholder is fixed in place by the forces that act on the vertebras. But the vertebras degenerate due to continuous axial and vertical loading and the placeholder leaves its prescribed position. If the placeholder sinks into the vertebra (due to high load, wear, poor bone quality, etc.), a space is created between the vertebras because the vertebras are no longer able to move toward one another since the spacing between them is fixed by the plate implants known from the prior art. The axial and vertical loads are now no longer conducted via the vertebras and the placeholder, but rather the force flow is conducted via the plate implant.

The forces that occur due to this settling or sinking process are great enough that the fastening screws that are provided for fixing the plate implants become loose. This renders the implant no longer functional and additional damage to bones and vertebras can occur. There is also the risk that the plate implant will break due to the high forces that occur. This can completely negate the actual function of the plate implant.

Thus one of the essential disadvantages of the plate implants known from the prior art is that the implants do not account for so-called settling.

OBJECT OF THE INVENTION

The object of the invention is to further develop plate implants according to the prior art such that in particular settling of bones and vertebras is compensated for when they are provided with a plate implant.

SUMMARY OF THE INVENTION

The present invention is intended to avoid the disadvantages of the prior art and to provide a plate implant that comprises at least two plates that are mounted such that they slide toward one another, their sliding being limited by formations including a clamping screw.

The clamping screw itself comprises a screw thread and a screw head, wherein, when the two plates are fitted together, the screw thread fits in the connector and the screw head fits in an elongated slot, specifically such that a clamping effect occurs between the screw head and the elongated slot and between the connector and the seat.

ADVANTAGES OF THE INVENTION

The invention follows a completely different path from that suggested by the prior art. In contrast to the prior art, in which relative sliding the plates is completely blocked after installation, due to the clamping effect performed, the settling causes the two plates to move toward one another against a defined clamping force. The clamping force is caused by the clamping screw tightening torque, but also by the clamping effect that the screw head of the clamping screw creates by engagement with the elongated slot.

Thus the bones or vertebras can move toward one another if the placeholder is no longer at the intended location. Because of this the force flow remains between the bones or vertebras and does not pass entirely through the plate implant itself, which ensures that the fastening screws are not loaded with forces so great that they can loosen or even detach from the bone or vertebras.

Another advantage of the invention is that with respect to its guide element the plate implant is designed such that when the plate implant is displaced elements of this implant do not slide across the vertebra or bone. This advantageously minimizes irritation to the periosteum.

Another of the advantages of the invention is that the plate implant can be produced from a desired material. Thus it is conceivable, for instance, that it can be produced from injection-molded plastic, in addition to titanium.

The size of the plates is selected to be very small. This is associated with the advantage that these individual plates can be placed precisely on the vertebras without creating an overhang (projecting beyond the surfaces of the vertebra). This is because it is known from the prior art that in particular plates selected that are too long and that are attached with screws through elongated slots provided in the plates move into the adjacent vertebra or into the intervertebral disk during the settling process and thus cause secondary damage.

Preferably provided are plate widths to less than 22 mm and plate thicknesses less than 2.5 mm.

In addition, compared to the prior art the plate implant in the present invention offers the advantage that it can be assembled prior to fitting it to the bone or vertebras and includes fixing means that enable simple temporary fixation to bone and vertebras so that it is possible, in a simple manner, to adjust the individual spacings and determine where best to attach the fastening screws.

Another advantage of the invention is comprised in that the plate implant is available as a set. Given the plates as a basic unit, it is possible to freely select the length of the plate implant on a case-by-case basis by interposing a different number of extension plates. The limited slide movement between each of the individual plates is retained. The individual plates and the extension plates nevertheless have a very small geometry so that the above-described secondary damages are prevented.

The extension plates preferably also comprise a plate-like base having bores for receiving fastening screws. Furthermore provided are seat for receiving a connector and a connector itself. Elongated slots for receiving another clamping screw and for limiting sliding are also provided. Thus a plate implant with a defined length can be produced from at least three different plates. The user can decide directly on-site which length is needed. This can be determined by the number of extension plates. Because of this there is no need for a high-cost inventory of different plate implants that have different lengths.

The plate implants themselves are curved in both their longitudinal and transverse extensions. In addition, because of their thickness they can be appropriately fitted to the outer surface of the bones or vertebras in that they can be shaped appropriately by the user.

However, this does not mean loss of the ability of the connector to freely slide in the seat so that it is possible to accommodate settling.

Due to the design of the individual plates and the extension plates it is possible for the user to follow the sequence for mounting the plate implant in a very simple manner because, due to the simple visual structure of plates and extension plates, assembly of the plates is self-explanatory and requires no further information.

In order to provide further support for this process, the individual plates are colored so that the user immediately perceives and can follow the sequence from the first plate, at least one extension plate, and the other plate. The individual plates can be assembled functionally with one another using a simple insertion system so that the result is individual sliding elements. Functionality can be tested with the first insertion.

By pre-fixing the clamping screw (applying incomplete tightening torque to the clamping screw), sliding of the plates relative to one another is possible but is limited to the corresponding freedoms of movement. The clamping force provided that is to act between the plates is not actuated until the clamping screw is screwed further into the connector.

Additional bores in each of the plates can be provided for pre-fixing the plates to the bone or vertebras so that it is possible to begin drilling the bone to attach the fastening screws.

The bores in the individual plates are selected such that the screws can be inserted polyaxially. This means that the fastening screws do not have to be inserted perpendicular to the individual plates. They can be screwed into the bone or vertebra at any desired angle. Preferably self-locking fastening screws are use. To this end for instance spreadable screw heads can be provided so that it is possible to clamp the screw with the plate immediately after it is fixed to the bone or vertebras.

BRIEF DESCRIPTION OF THE FIGURES IN THE DRAWINGS

EMBODIMENTS OF THE INVENTION

Figure 1:
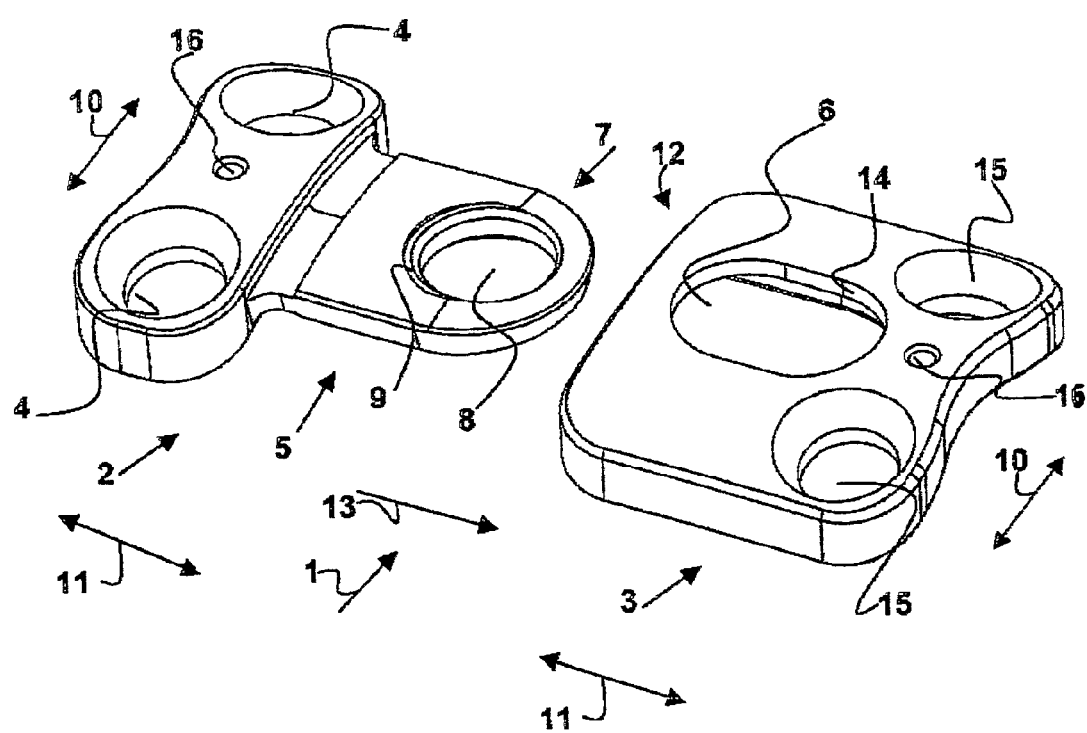
FIG. 1 is a perspective elevation of the plate implant, comprising a first plate and a second plate, the two plates not being connected to one another.

FIG. 1 illustrates the basic principle of the plate implant 1. This plate implant 1 comprises a first end plate 2 and another end plate 3. The two end plates 2 and 3 have different shapes.

The first plate 2 has bores 4 for fastening screws (not shown in greater detail). Furthermore, a connector 5 is provided that fits in a seat 6 for the other, second plate 3. The connector 5 is shaped like a tongue and its cross-section is smaller than the other element of the plate 2. The connector 5 is also not as thick as the other element of the plate 1.

A bore 8 is provided on the outer end 7 of the connector 5. This bore 8 preferably also has a female screwthread 9.

The first plate 2 is curved both in the direction 10 of its transverse extension and in the direction 11 of its longitudinal extension so that it can be fitted to a vertebra or bone.

As stated above, the tongue-like connector 5 is designed to fits in the seat 6 of the second plate 3. To this end the second plate 3 has as seat 6 within the base body of the second plate 3 a groove 12 that is shaped such that the tongue-like connector 5 can be inserted into the seat 6 in the direction of the arrow 13. Preferably a dovetail guide is provided for a precise, nearly zero-clearance fit. The tongue-like connector 5 is designed such that on the side facing the vertebra or bone it is not flush with the bottom of the plates 2 and 3. An offset is provided in order to prevent this connector 5 from sliding on the surface of the bone or vertebra when being slid.

The second plate 3 furthermore has a longitudinally extending slot 14 that aligns with the bore 8 of the connector 5 when the first plate 2 is inserted.

The second plate 3 furthermore also has bores 15 for receiving fastening screws that are not shown in FIG. 1. Each of the plates 2 and 3 has bores 16 that are significantly smaller in diameter than the other bores 4 and 15. These bores 16 are intended for pre-fixing on the bone or vertebras the position of the plate 2 and 3 before it is mounted with the fastening screws.

The second plate 3 is almost square and also has a radius of curvature in both its longitudinal extension 11 and its transverse extension 10. In addition, it is also flexible in these directions so that it can be fitted to the outside surface of vertebras and bones.

Figure 2:
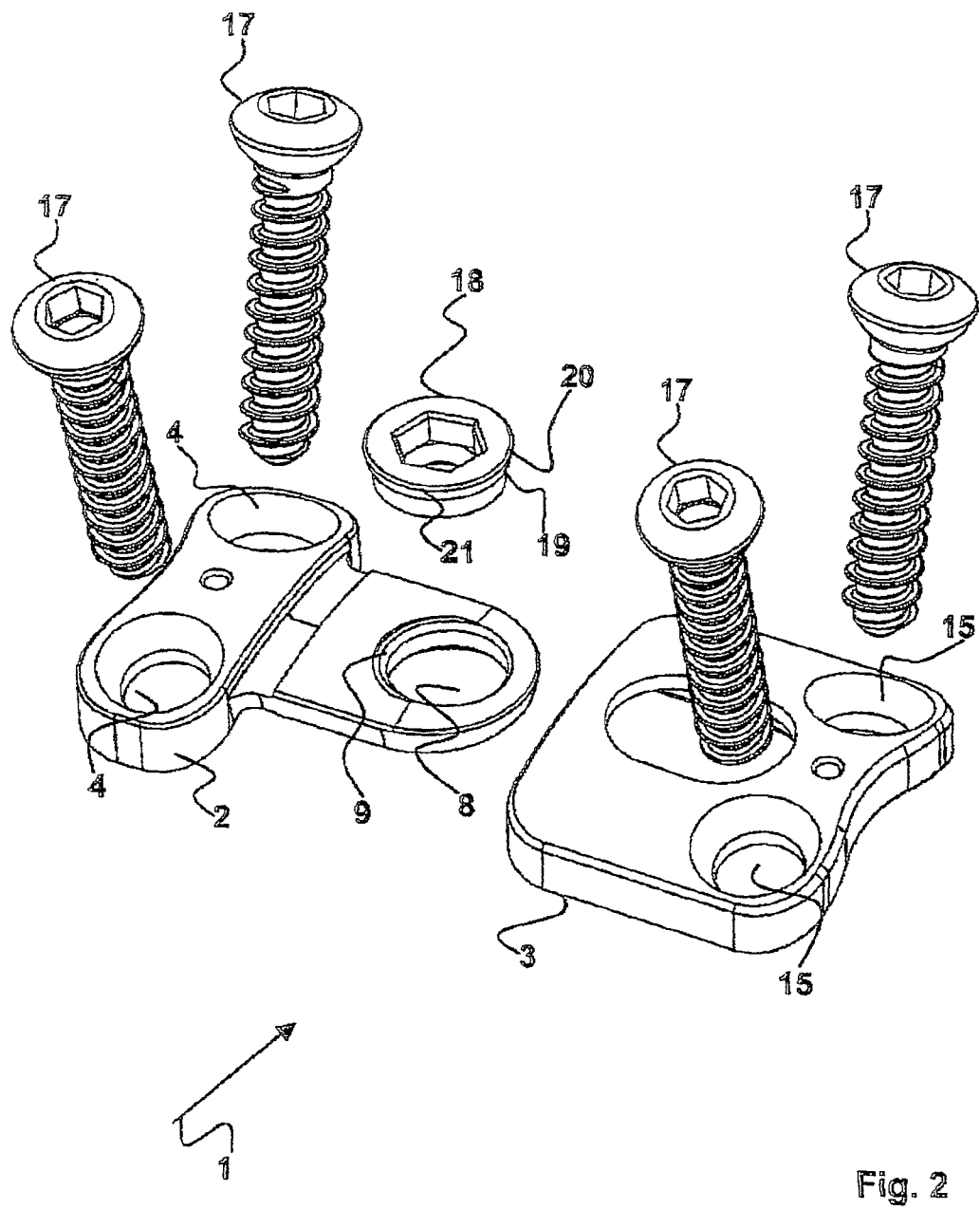
FIG. 2 is a perspective elevation of the plates shown in FIG. 1, but illustrating the fastening screws and the inventive clamping screw.

FIG. 2 shows the basic principle for the plate implant 1 in accordance with FIG. 1. Fastening screws 17 that can be inserted polyaxially into the bores 4, 15 are shown for the bores 4 and 15. Polyaxially means that they do not have to be installed perpendicular to the surface of the plate 2 and 3, but rather they can be inserted depending on the characteristics of the structure they are used for.

In addition a clamping screw 18 is provided that can be screwed into the thread 9 of the bore 8. The clamping screw 18 is embodied such that it also has a screwthread 19 that fits with the screwthread 9 of the bore 8. In addition, on its screw head the clamping screw 18 has an enlarged portion 20 that is preferably wider than the other part of the thread 19. This enlarged portion 20 has a bevel 21 that widens outward so that the diameter of the clamping screw 18 increases away from the thread 19.

Figure 3:
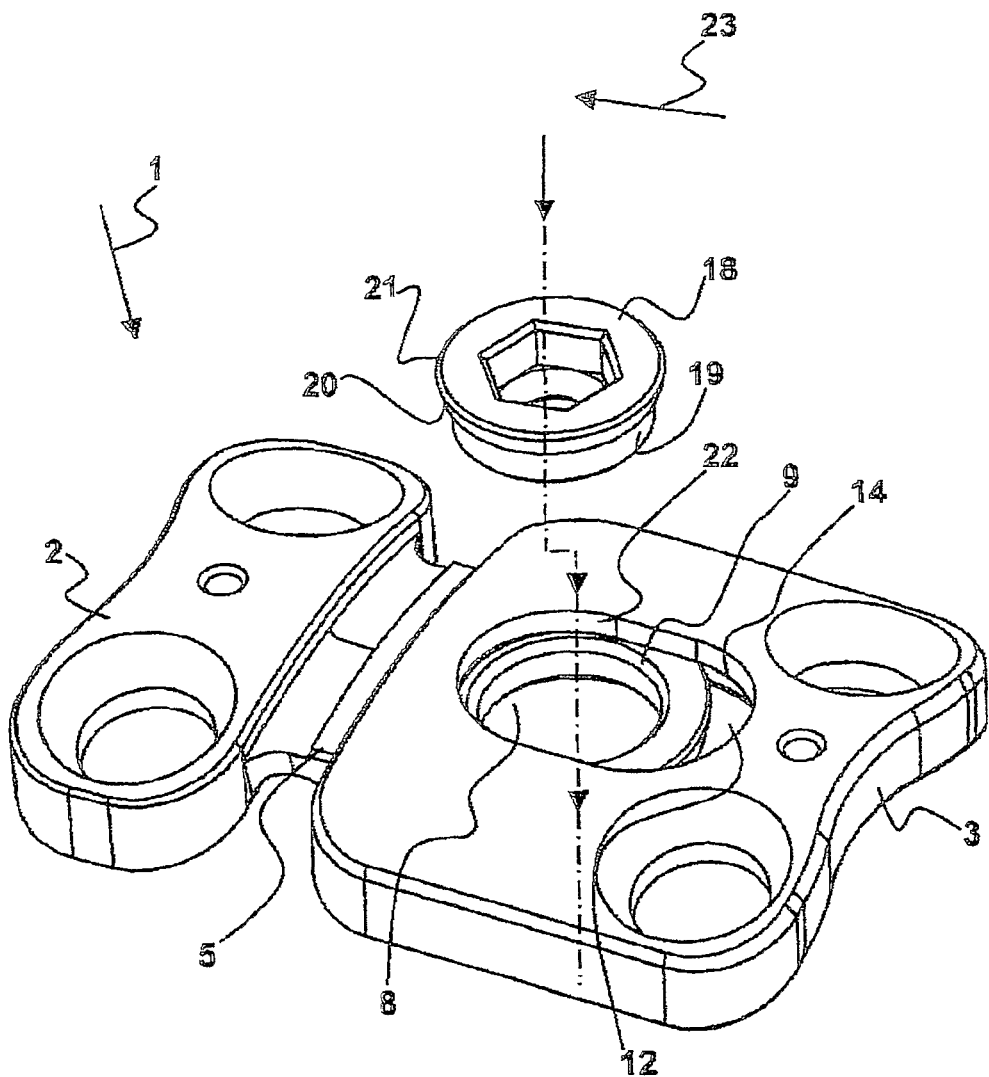
FIG. 3 is a perspective view of a plate implant, comprising two plates and a clamping screw that is not yet fixed.

FIG. 3 shows how the clamping screw 18 functions in conjunction with the plate implant 1. When the plates 2 and 3 are assembled, it is inserted through the elongated slot 14 of the second plate 3 and the thread 19 of the clamping screw 18 comes into contact with the thread 9 of the bore 8 of the connector 5. The enlarged portion 20 comes into contact with side flanks 22 of the elongated slot 14 such that a first clamping effect occurs between the clamping screw 18 and the plate 3. A clamping effect also occurs by screwing the clamping screw 18 into the bore 8 in that the connector 5 presses inside the groove 12 against an inner surface of the second plate 3 and a clamping effect occurs here. It is expressly noted that the two plates 2 and 3 and the clamping screw 18 are embodied such that no blocking of sliding movement is intended in or against the direction of the arrow 23. The goal is to attain a clamping effect that makes it possible for the first plate 2 to slide against the second plate 3 against a defined force.

In the position illustrated in FIG. 3, the clamping screw 18 is screwed in so that the appropriate clamping effect is attained. If a force is exerted on the plate implant 1 due to so-called settling, the plates 2 and 3 move toward one another in the direction of the arrow 23. However, the forces must be great enough that the clamping effect created by the clamping screw 18 is overcome. Only then is there any movement in the direction of the arrow 23.

In another illustrated embodiment the elongated slot 14 can also advantageously be conical so that it tapers in the direction of the arrow 23. This means that the clamping force grows as settling increases. This also means that the forces must be greater in order to cause a corresponding displacement in the direction of the arrow 23.

Figure 4:
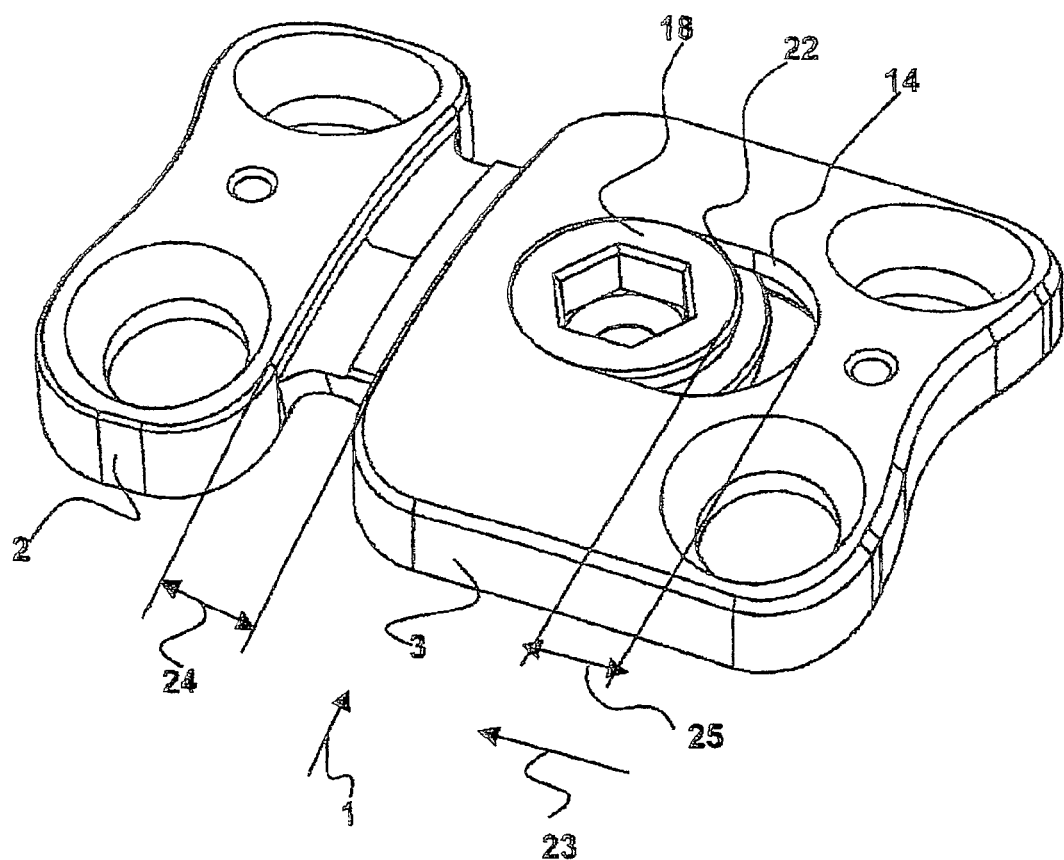
FIG. 4 is a perspective elevation of the assembled plate implant in accordance with FIG. 3, but with the clamping screw mounted.

FIG. 4 shows the basic shape of the plate implant 1, previously illustrated in FIGS. 1 and 2, when assembled. The clamping screw 18 engages against the side flanks 22 of the elongated slot 14. The view in FIG. 4 illustrates the starting position. Settling causes displacement in the direction of the arrow 23, specifically the maximum path, which is limited by the spacing 24 from the one part of the first plate 2 to the second plate 3 or by the spacing 25.

Figure 5:
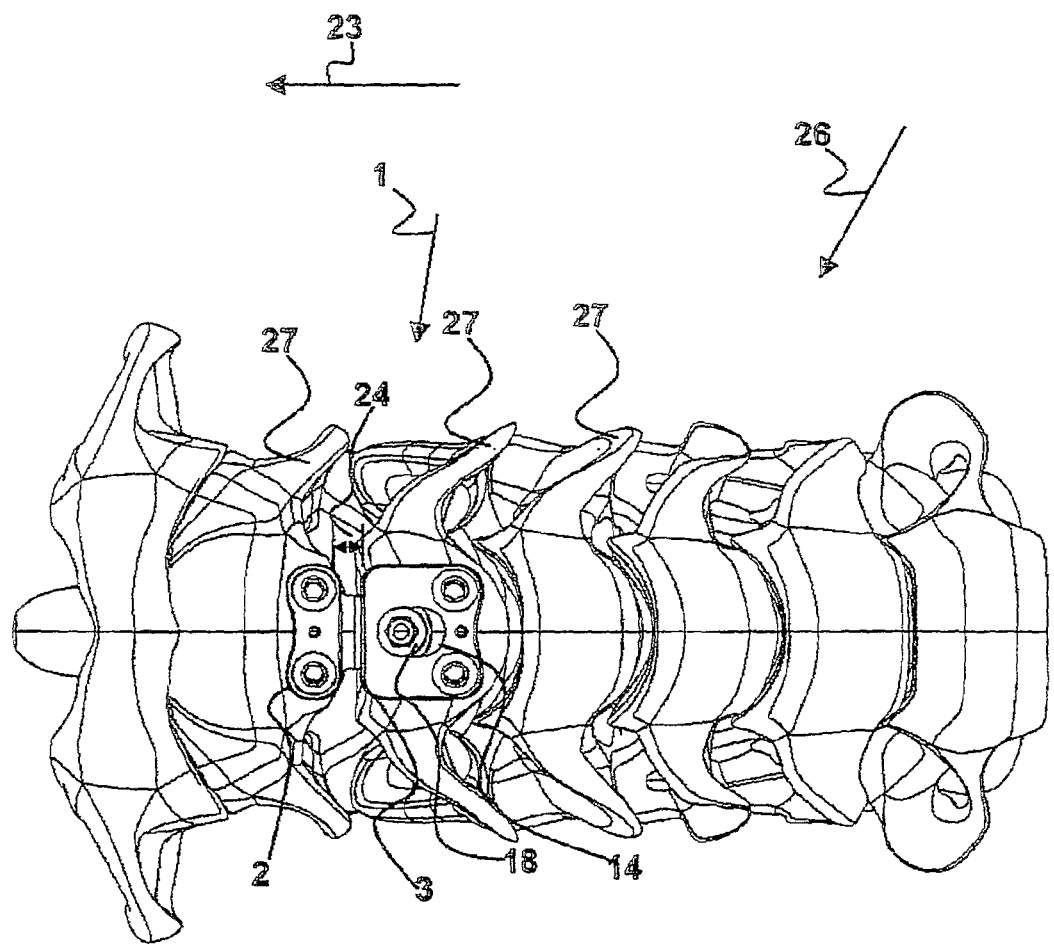
FIG. 5 is a top view of an installed plate implant comprising two plates in an unsettled region of the cervical spine.

FIG. 5 is a top view of a basic unit of the plate implant 1. The top view is of a part of a spinal column 26 that comprises a plurality of vertebras 27. In the illustrated embodiment shown here, the first plate 2 is secured to a first vertebra 27, the second plate 3 being secured to the adjacent vertebra 27. The two plates 2 and 3 have the spacing 24 that was freely selected in order to compensate for settling by the two vertebras 27. The clamping screw 18 is engaged through the elongated slot 14 such that it is on the side facing the first plate 2 so that displacement of the first plate 2 relative to the second plate 3 against the direction of the arrow 23 is possible or displacement of the second plate 3 relative to the first plate 2 in the direction of the arrow 23 is possible.

Figure 6:
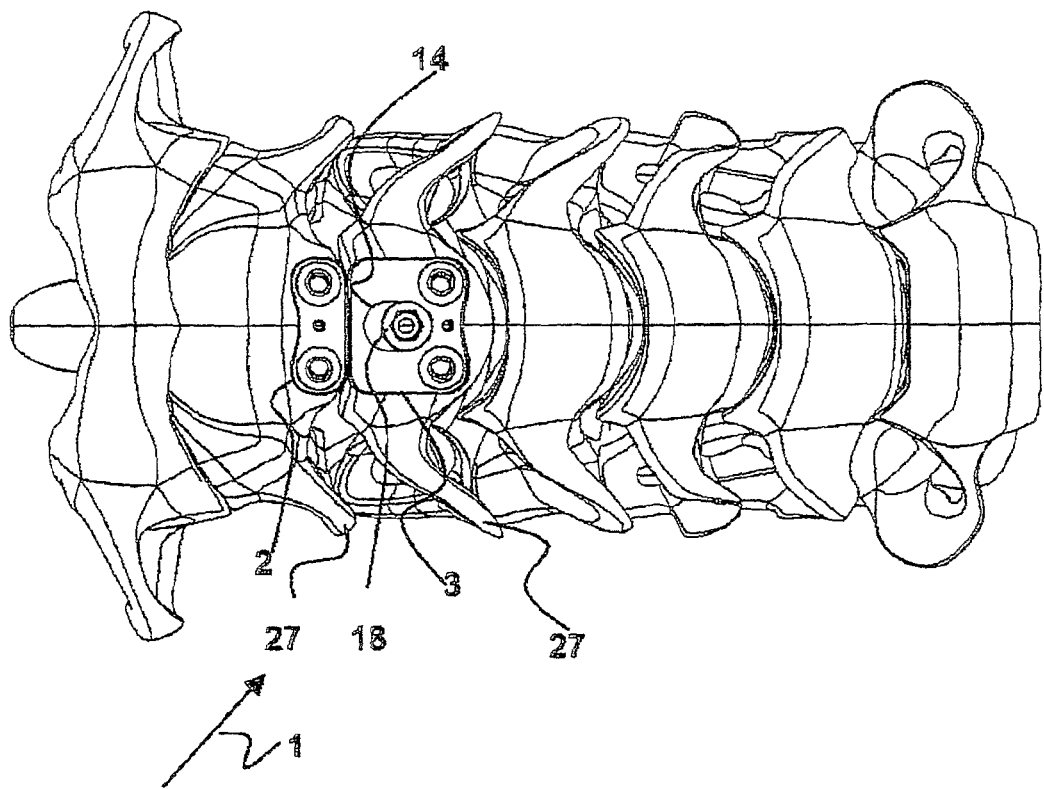
FIG. 6 is a top view of an installed plate implant, comprising two plates in a settled region of the cervical spine.

As FIG. 6 shows, settling has occurred and the two plates 2 and 3 have moved toward one another. The clamping screw 18 has slid inside the elongated slot 14 and reached its final end position. In this position, the vertebras 27 are very close to one another so that it is furthermore assured that the force flows via the vertebras themselves, not via the plate implant 1. The plate implant 1 furthermore retains its strength with respect to the vertebra 27 since the forces do not act on the fastening screws 17.

Figure 7:
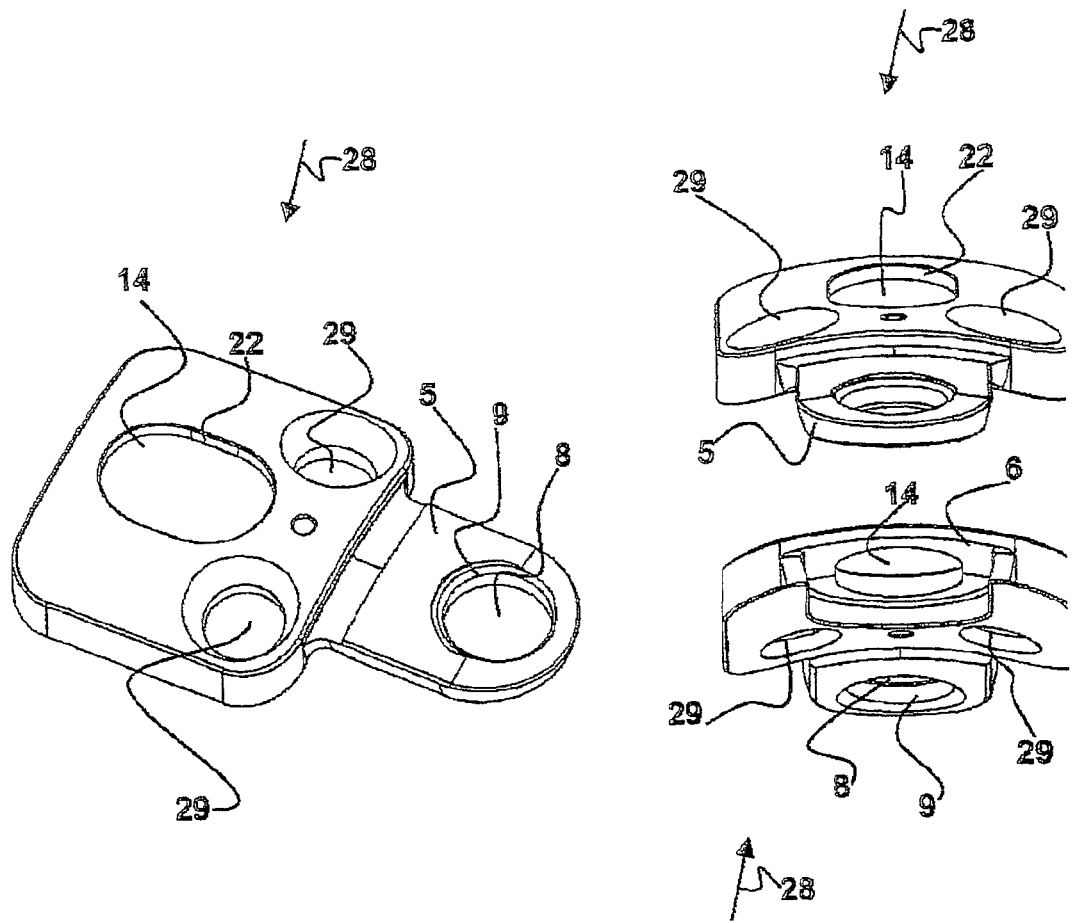
FIG. 7 is three perspective view of an extension element.

FIG. 7 provides a plurality of perspective views of an extension plate 28. An extension plate likewise comprises a nearly square base body with a connector 5 extending from one side. This connector 5 is designed as already provided for the first plate 2 in accordance with FIG. 1. It is shaped like a tongue and at its end has a bore 8 having a female thread 9. The base body 28 of the extension plate furthermore has two bores 29 that receive fastening screws not shown in the drawing. An elongated slot 14 is furthermore provided in the base body. This elongated slot is the same as the elongated slot 14 that is known from the second plate 3. It also has a longitudinal groove and defined side flanks 22. The extension plate 28 furthermore has a seat 6. This seat 6 is configured in a manner already familiar from the second plate 3. It receives the connector 5.

Figure 8:
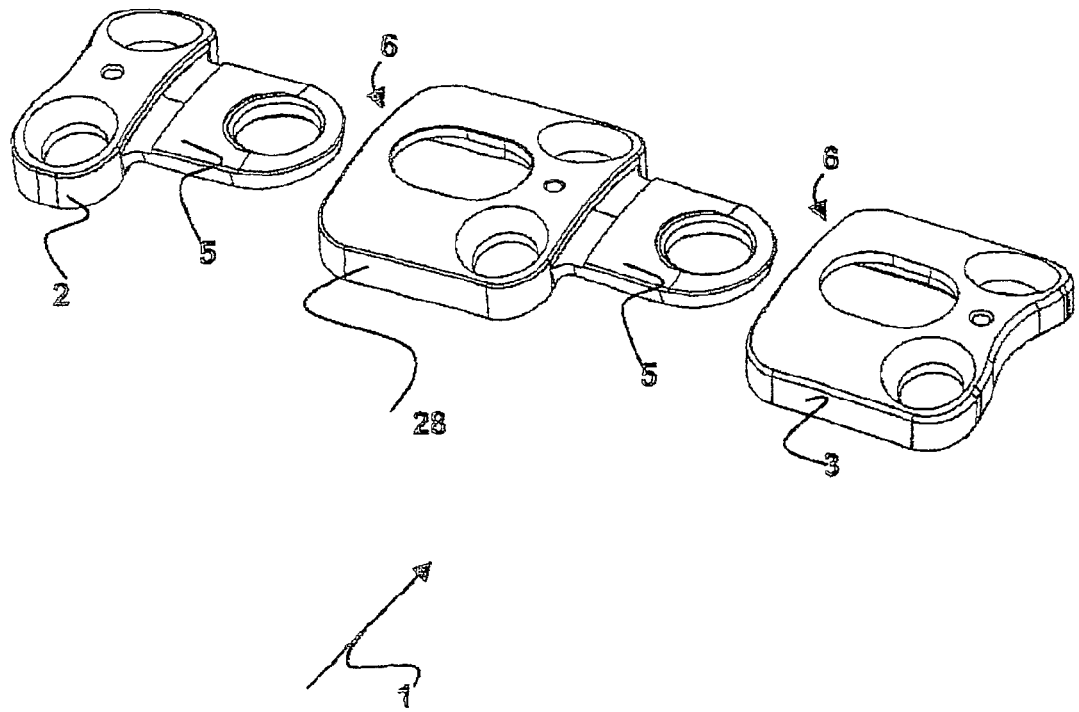
FIG. 8 is a perspective view of an illustrated embodiment of a plate implant comprising two plates and one extension plate.

FIG. 8 is a perspective view of how such an extension plate 28 is used. The extension plate 28 can be inserted, like a link in a chain, between the first plate 2 and the second plate 3. This assembly forms another possible illustrated embodiment of a plate implant 1. A plurality of such extension plates 28 can also be inserted as needed, but a first plate 2 must always be at the beginning of the "chain" and a second plate 3 must always be at the end of the "chain." These two plates 2 and 3 form the ends of the "chain."

Figure 9:
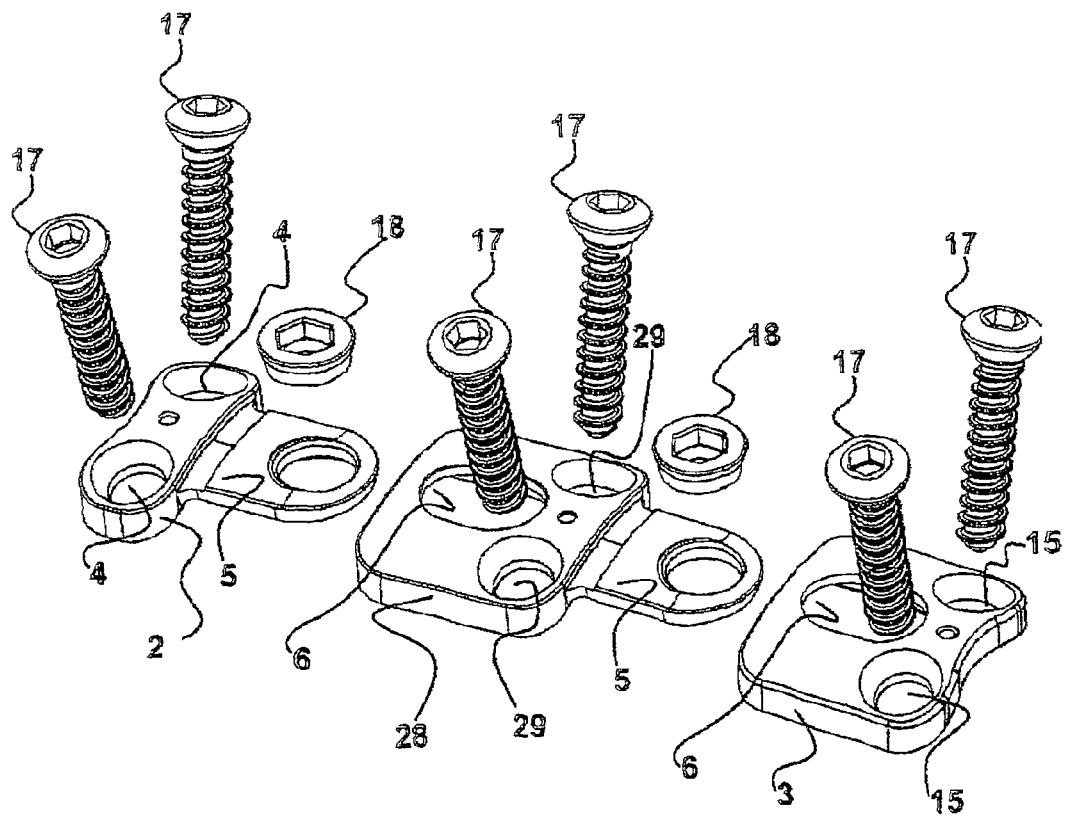
FIG. 9 is a perspective view of the plates with the extension plate, together with fastening screws and clamping screws.

FIG. 9 shows the plate implant 1 shown in FIG. 8 together with the extension plate 28 along with fastening screws 17 and also clamping screws 18. Each of the plates has at least two bores 4, 15, 29, into which the fastening screws 17 can be introduced polyaxially. The appropriate clamping force is the result of the cooperation of clamping screws 18 with the connection elements 5 and the seat 6.

Figure 10:
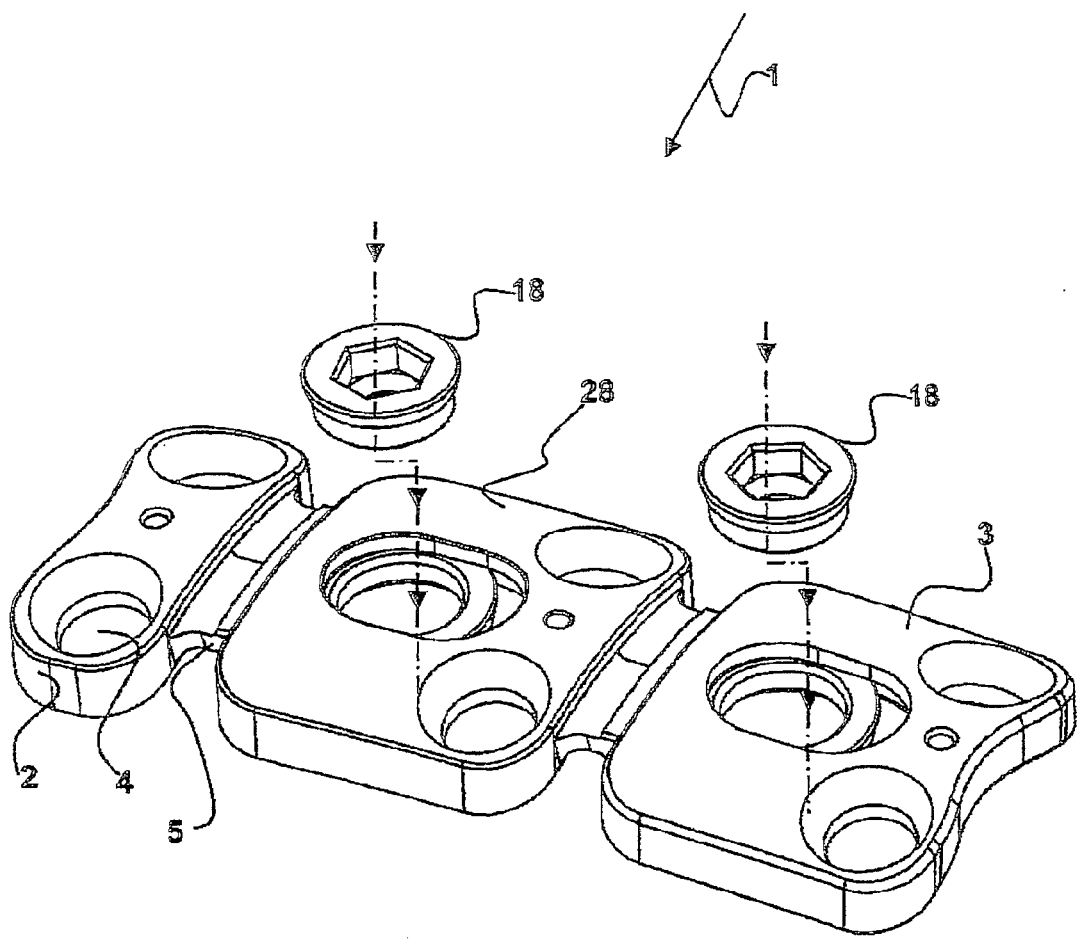
FIG. 10 is a perspective view of an assembled plate implant comprising two plates and one extension plate, with clamping screws that have not been inserted yet.
Figure 11:
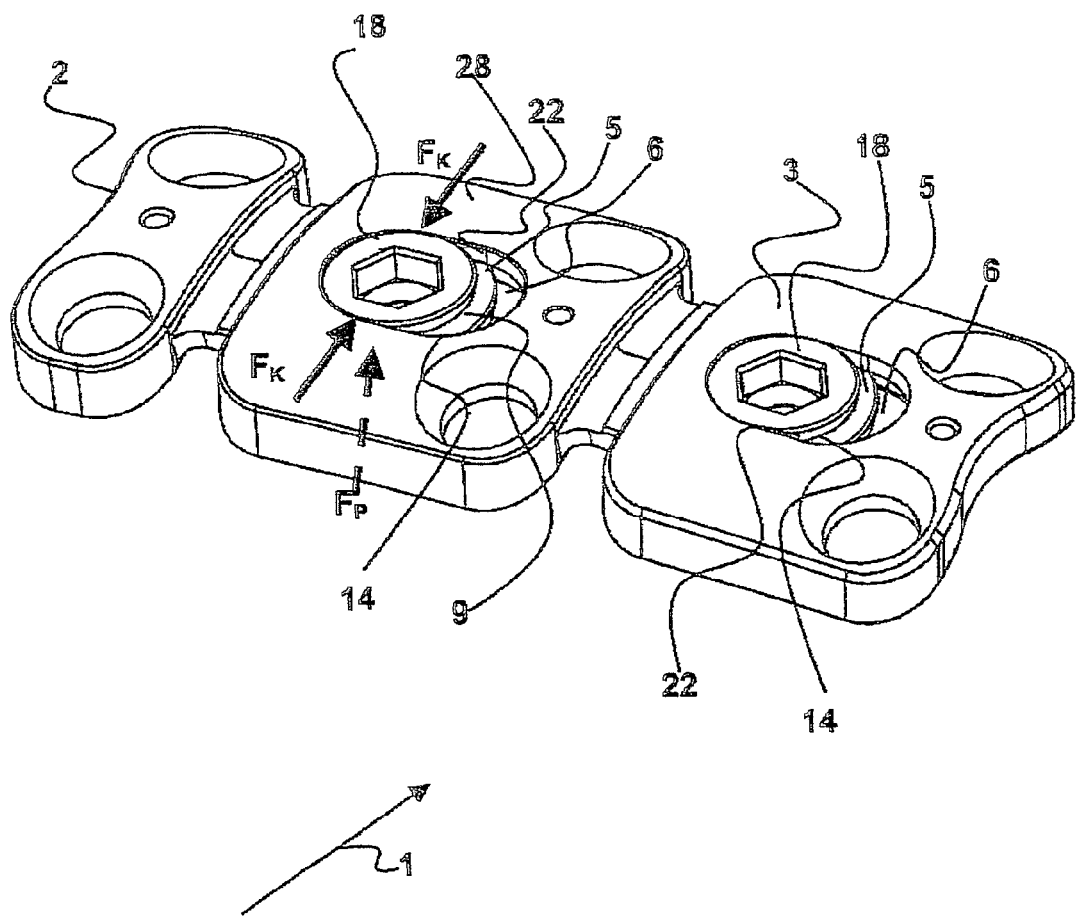
FIG. 11 is a perspective view of an assembled plate implant comprising two plates and one extension plate, with clamping screws inserted.

FIGS. 10 and 11 show the assembly and construction of one illustrated embodiment of a plate implant 1 as has been explained with reference to FIGS. 8 and 9.

The view shown in FIG. 10 illustrates a sliding movement that has not been limited. In contrast to FIG. 10, in FIG. 11 the clamping screws 18 have each been screwed in such that the screw heads of the clamping screws 18 engage the side flanks 22 of the respective elongated slots 14. The clamping forces F created because of this are shown in an exemplary manner for all ways in which each clamping screw 18 fits in an elongated slot 14. First of all, there are clamping forces $F_K$ that the clamping screw 18 exerts on the side flanks 22 of the elongated slot 14. Secondly, there are clamping forces $F_P$ that occur due to the clamping screw 18 being screwed into the bore 8 of the connector 5. Because of the fact that the screw head of the clamping screw 18 bears against the side flanks 22 of the longitudinal bore, the connector 5 is pulled to the interior of the seat 6 so that it flattens. The other clamping force $F_P$ occurs because of this.

Figure 12:
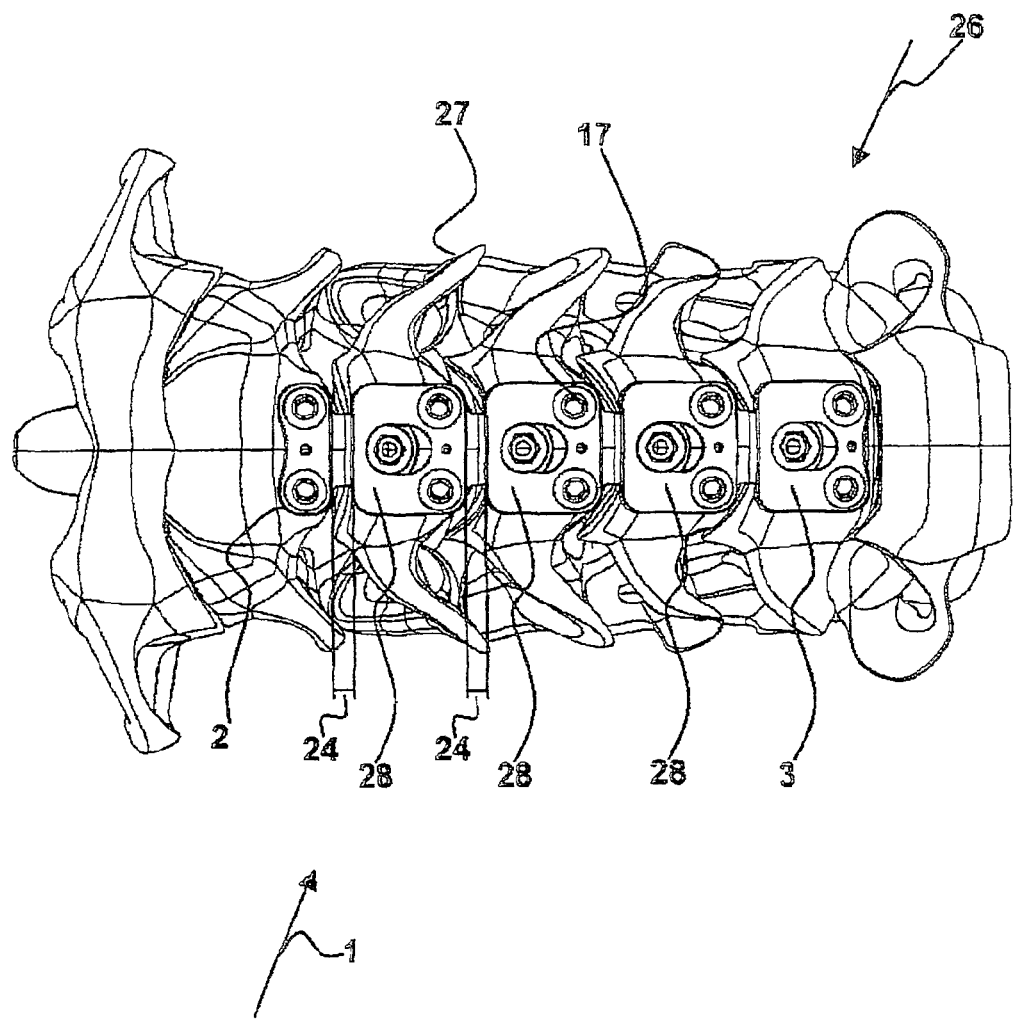
FIG. 12 is a top view of a mounted plate implant comprising two end plates and three extension plates, mounted on an unsettled cervical vertebra.
Figure 13:
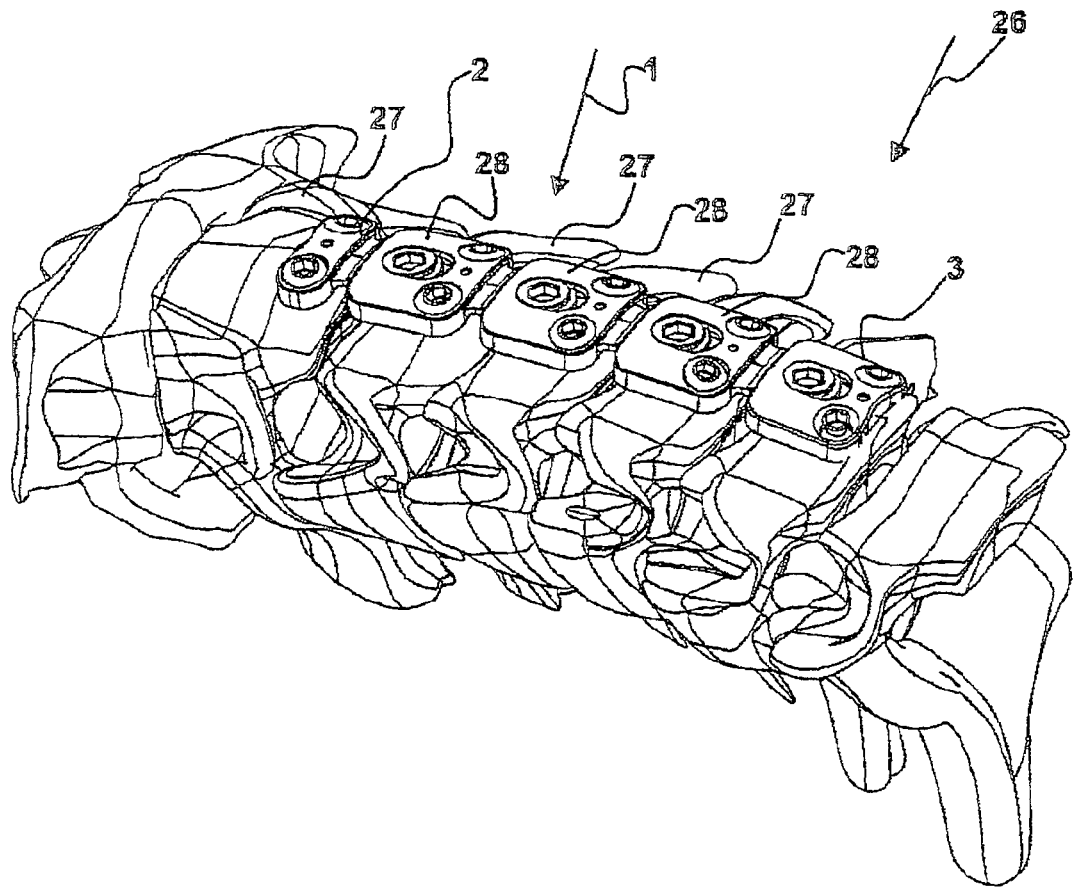
FIG. 13 is another perspective view of a mounted plate implant, comprising two end plates and three extension plates, mounted on an unsettled cervical vertebra.

FIGS. 12 and 13 show an exemplary application that includes a plate implant 1 that comprises the first plate 2 and the second plate 3 and three extension plates 28. The spacings between the extension plates 28 are selected such that the fastening screws 17 find optimum purchase in the vertebras 27 of the vertebral column 26 shown here. A spacing 24 created between the individual plates is needed to compensate for the above-described settling.

The following illustrates the manner in which the clamping effect of the plate implant 1 functions. In particular greater detail will be provided on the effect of the clamping screw 18 when it fits in the connector 5 and the seat 6.

Figure 14:
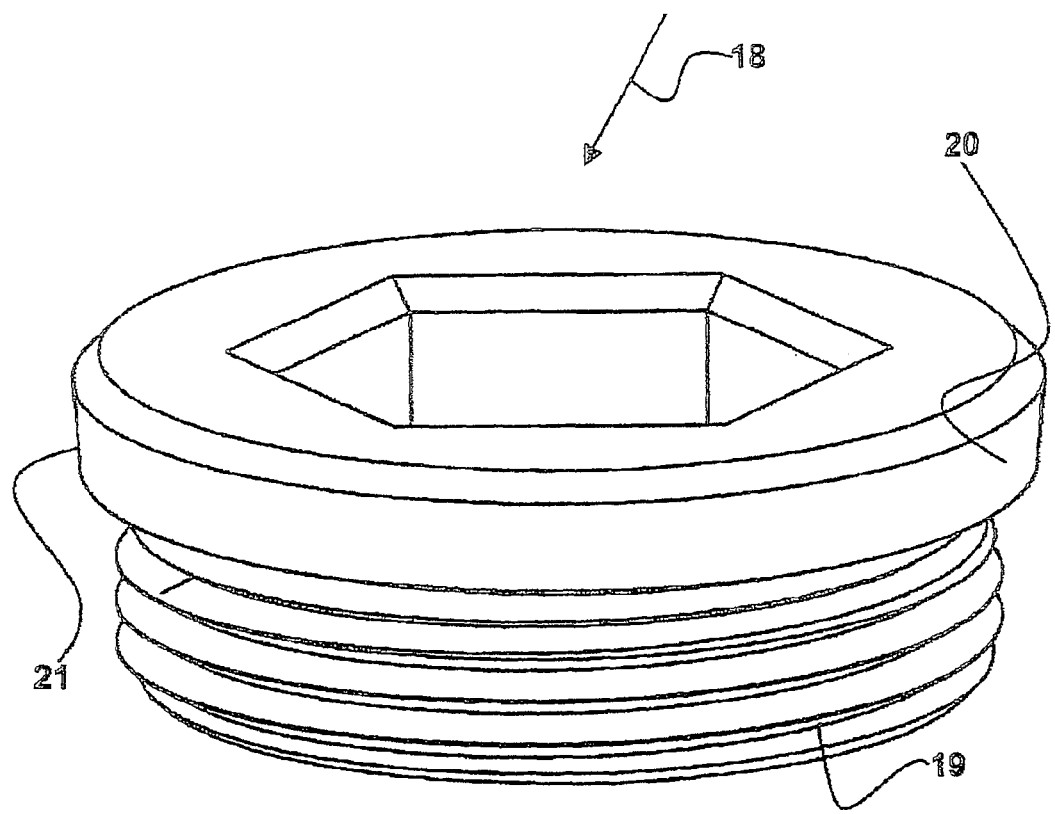
FIG. 14 is a perspective view of the clamping screw.

FIG. 14 is a perspective view of the clamping screw 18 that has already been used in the previous figures. The clamping screw essentially has two parts, specifically a first screw-head part head and another part, specifically a threaded part. The part of the screw thread includes a thread 19 that is conventional as a rule. However, it can also be a fine pitch thread so that corresponding clamping forces can be effected with just a few turns.

The screw head has a special shape. It has a circumferential enlarged portion 20 whose diameter is at least the same as that of the screw thread. Preferably the screw head is larger than the thread 19. The enlarged portion 20 has a certain thickness. The thickness is designed such that it is the all the way around. However, it has a slight frustoconicity 21 that it angles inward from the side remote from the thread 19 to the side close to the thread 19.

The clamping screw 18 furthermore has a turning tool. In the embodiment illustrated resented here the turning tool is a hexagonal-section body that can be inserted into the screw head in a simple manner. A positive force-transmitting fit results after it has been introduced so that the appropriate turning movement or the appropriate torque can be applied.

Figure 15:
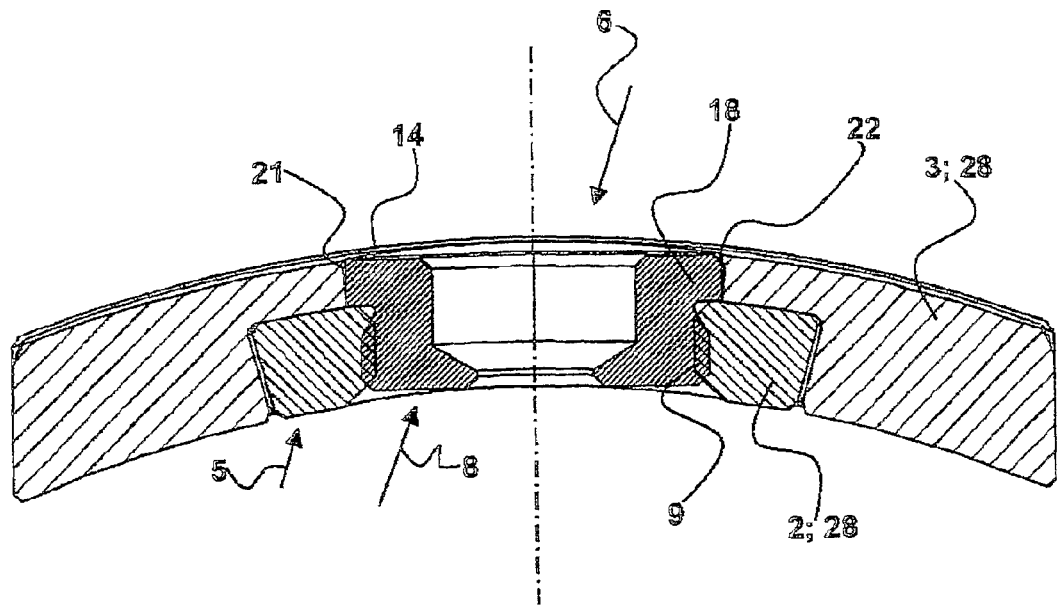
FIG. 15 is a section through a plate implant at the clamping screw.

FIG. 15 shows a section through a plate implant 1. The section is representative of all embodiments of the inventive plate implant 1, and specifically that of the basic unit comprising a first plate 2 and a second plate 3, and the illustrated embodiments that have one or a plurality of extension plates 28. The connection for the individual plates is always the same. As a rule it comprises a connector 5 that is guided in a seat 6. Preferably appropriate clearance is provided laterally so that it is possible to easily guide the connector 5 within the seat 6. The section in accordance with FIG. 15 now shows the base of either the second plate 3 or an extension plate 28. The connector 5 has already been inserted into this base and pushed far enough therein that the bore 8 of the connector 5 aligns with the elongated slot 14 of the base.

Furthermore, the clamping screw 18 has already been inserted into the base. The thread 19 of the clamping screw 18 has been completely screwed into the bore 8, which has a corresponding thread 9. The side surfaces 21 of the clamping screw 18 bear against the side flanks 22 of the elongated slot 14.

Figure 16:
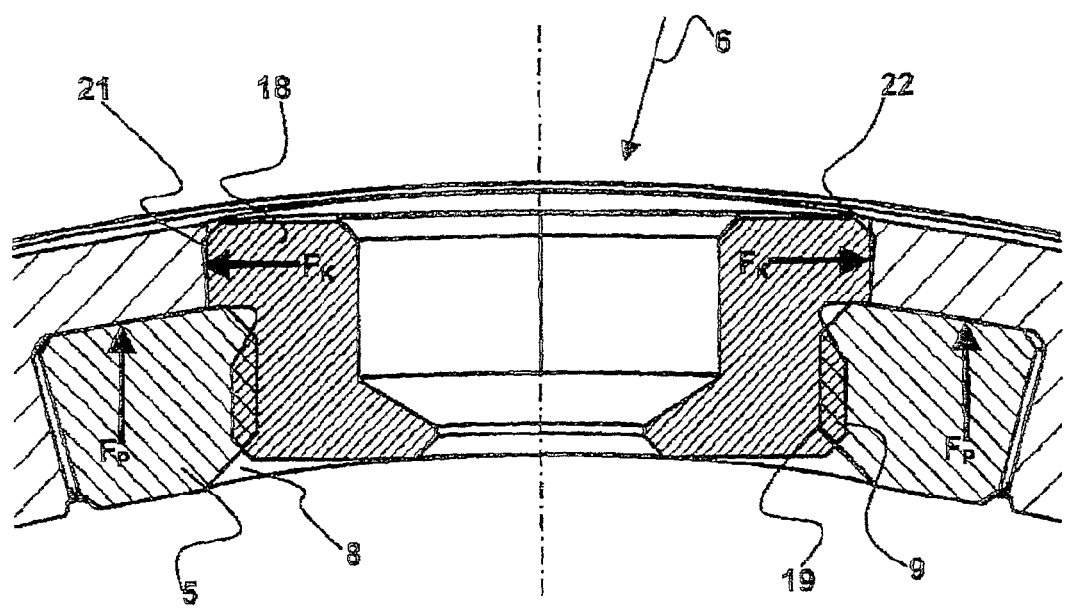
FIG. 16 is a large-scale view of the clamping region in accordance with FIG. 15.
Figure 17:
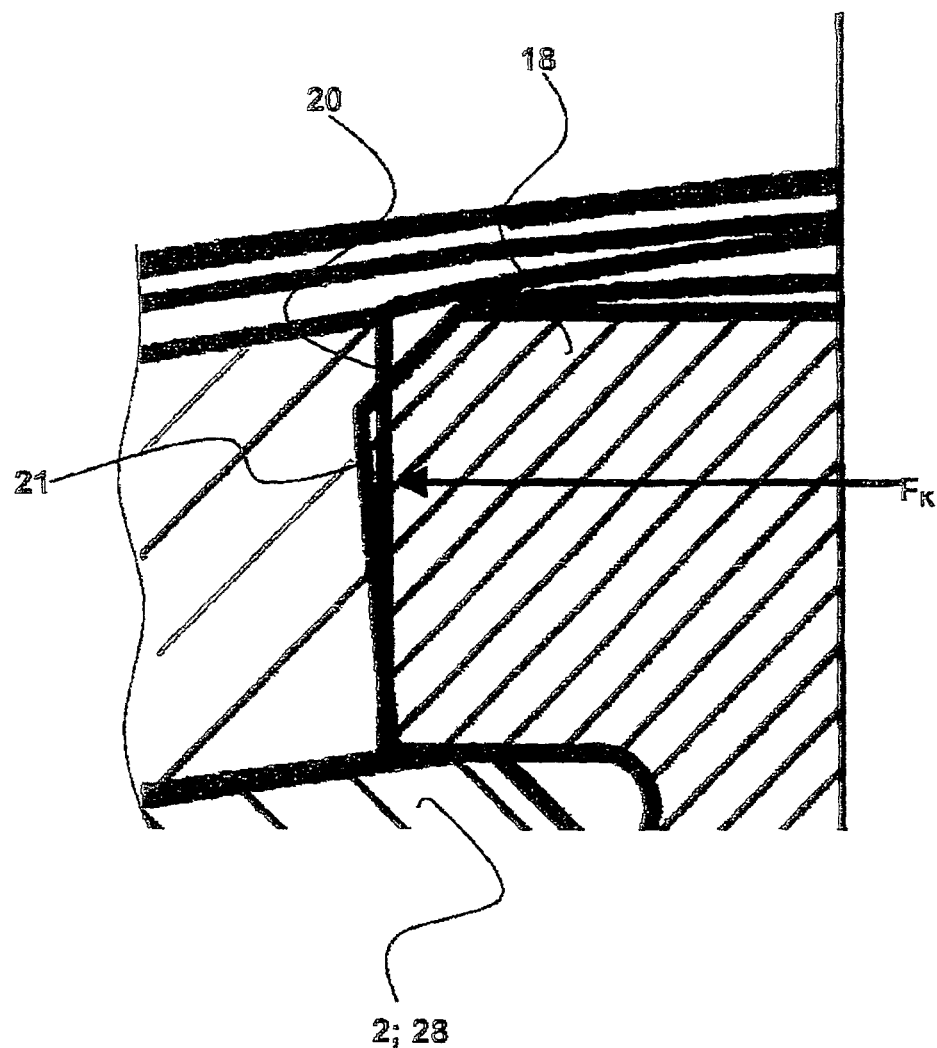
FIG. 17 is another large-scale view of the clamping region of the elongated slot.

FIG. 16 is an enlargement of FIG. 15. Compared to FIG. 15, the clamping forces that are active when the clamping screw 18 has been screwed in are also illustrated. The first clamping force that occurs is the clamping force that is caused when the clamping screw is screwed in and is in contact with the connector 5. Screwing it in causes the connector 5 to be pressed directly against the interior of the seat 6 so that clamping forces $F_P$ occur. Another clamping force occurs because the bevel 21 of the clamping screw 18 fits against the side flanks 22 of the elongated slot 14. As can be seen in particular from FIG. 17, the side flank on the side facing away from the thread 19 projects slightly so that there is a resultant clamping or wedge effect. Clamping forces $F_K$ occur. When the elongated slot has a uniform, symmetrical design, the clamping forces $F_K$ are nearly equal. However, if the elongated slot 14 tapers, the clamping forces increase as the end stop is neared (path limitation for slide movement).

Thus, there is a dual safety effect due to the clamping forces $F_K$, $F_P$ that occur. The clamping forces that occur are also oriented in different directions so that they cannot counteract one another.

Selecting the materials and surfaces appropriately can ensure that the possible sliding movement is not blocked and that it is always possible to slide the connector within the seat against the selected clamping force.

Due to the inventive design of the plate implant, which comprises at least one first plate and one second plate, but preferably also extension plates interposed between the first plate and the second plate, a plate implant has been created that can be used universally for osteosynthesis. This plate implant is distinguished in particular in that it compensates for so-called settling, which occurs when the stiffened bone elements settle, so that the force flow that is normally absorbed by the bones is also transmitted further via the bones so that functional overload of the plate implant is prevented.

The simple design and modular principle makes it possible to select plate implants having different lengths and sizes. By simply inserting one unit into another it is possible to perform prefixation without any problems and without a great deal of complexity so that for the user adaptation proceeds in a simple manner, in particular for cervical vertebras.

The invention claimed is:

1. A plate implant for use in osteosynthesis between a pair of adjacent vertebrae, the implant comprising:
   at least one first end plate having a longitudinally extending tongue-shaped connector formed with a threaded bore, the first end plate being formed with holes for receiving screws fastening the first end plate to one of the vertebrae;
   at least one second end plate having a longitudinally extending seat for receiving the connector and holes for receiving screws fastening the second end plate to the other of the vertebrae, mutually engaging surfaces of the seat and extension being smooth, the second end plate being formed at the seat with a longitudinally elongated tapered slot having longitudinally extending side flanks, each end plate being able to slide longitudinally toward and away from the other end plate with sliding of the connector in a longitudinal direction in the seat between a starting position with the end plates spaced longitudinally apart and an end position with the end plates longitudinally closely juxtaposed;
   formations on the end plates that engage each other in the end position and limit longitudinal sliding of the end plates toward one another; and
   a clamping screw formed with a screwthread fittable in the threaded bore of the connector, the screw having a screw head and, when the two end plates are fitted together, the screwthread fitting with the threaded bore of the connector and the screw head fitting in the elongated slot with the head bearing on the side flanks such that a clamping effect occurs between the screw head and the elongated slot and between the connector and the seat, the two end plates and the clamping screw being constructed such that the clamping effect does not completely block relative sliding in or against the longitudinal direction while increasing in a direction corresponding to longitudinal separation of the plates due to the transverse convergence of the side flanks, thereby permitting relative limited longitudinal separation of the respective vertebrae with increasing resistance to separation as the end plates separate longitudinally.

2. The plate implant according to claim 1, further comprising:
   at least one extension plate between the first end plate and the second end plate, the extension plate having
   bores for receiving fastening screws,
   a seat for receiving the connector of the first end plate,
   an extension-plate connector, and
   an elongated slot for receiving another clamping screw and for limiting sliding.

3. The plate implant according to claim 2 wherein the end plates and the extension plate are made of plastic.

4. The plate implant according to claim 2 wherein the end plates and the extension plate are curved in both their longitudinal extension and in their transverse extension.

5. The plate implant according to claim 1 wherein the tongue-shaped connector is made on a face turned toward the respective vertebra or bone to be inset from an inner face of the first end plate.

\* \* \* \* \*